(12) United States Patent
Huter et al.

(10) Patent No.: US 7,108,707 B2
(45) Date of Patent: *Sep. 19, 2006

(54) HINGED SHORT CAGE FOR AN EMBOLIC PROTECTION DEVICE

(75) Inventors: Benjamin C. Huter, Murrieta, CA (US); Kevin M. Magrini, Temecula, CA (US); John E. Papp, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 304 days.

This patent is subject to a terminal disclaimer.

(21) Appl. No.: 10/600,817

(22) Filed: Jun. 20, 2003

(65) Prior Publication Data

US 2004/0006366 A1    Jan. 8, 2004

Related U.S. Application Data

(63) Continuation of application No. 09/944,633, filed on Aug. 31, 2001, now Pat. No. 6,592,606.

(51) Int. Cl.
*A61M 29/00* (2006.01)
(52) U.S. Cl. ..................................... 606/200
(58) Field of Classification Search ............... 606/200, 606/191, 113, 114, 159, 127; 600/434, 585; 604/528

See application file for complete search history.

(56) References Cited

U.S. PATENT DOCUMENTS

| 5,108,368 A | * | 4/1992 | Hammerslag et al. | ...... 604/528 |
| 6,152,946 A | | 11/2000 | Broome et al. | |
| 6,171,327 B1 | | 1/2001 | Daniel et al. | |

* cited by examiner

*Primary Examiner*—Kevin T. Truong
(74) *Attorney, Agent, or Firm*—Fulwider Patton LLP

(57) ABSTRACT

A filtering device for capturing and removing embolic debris from a body vessel and a system for insertion and removal of the filtering device to facilitate an interventional procedure in a stenosed or occluded region of a body vessel. The filtering device is adapted to be expandable in the body vessel, allowing blood to pass therethrough while maintaining apposition with the body vessel wall and capturing embolic material released into the bloodstream during the interventional procedure, and to be collapsible to remove the captured embolic material from the body vessel. The filtering device includes a guide wire, an expandable cage assembly secured to the guide wire, filter material secured to the expandable cage assembly, and at least one hinge, the hinge allowing the expandable cage assembly to bend independent from the guide wire. The system, which includes a delivery sheath and filtering device, is adapted to retain the expandable cage assembly in a collapsed condition and deliver and deploy the filtering device at a location in the body vessel distal the treatment site.

11 Claims, 8 Drawing Sheets

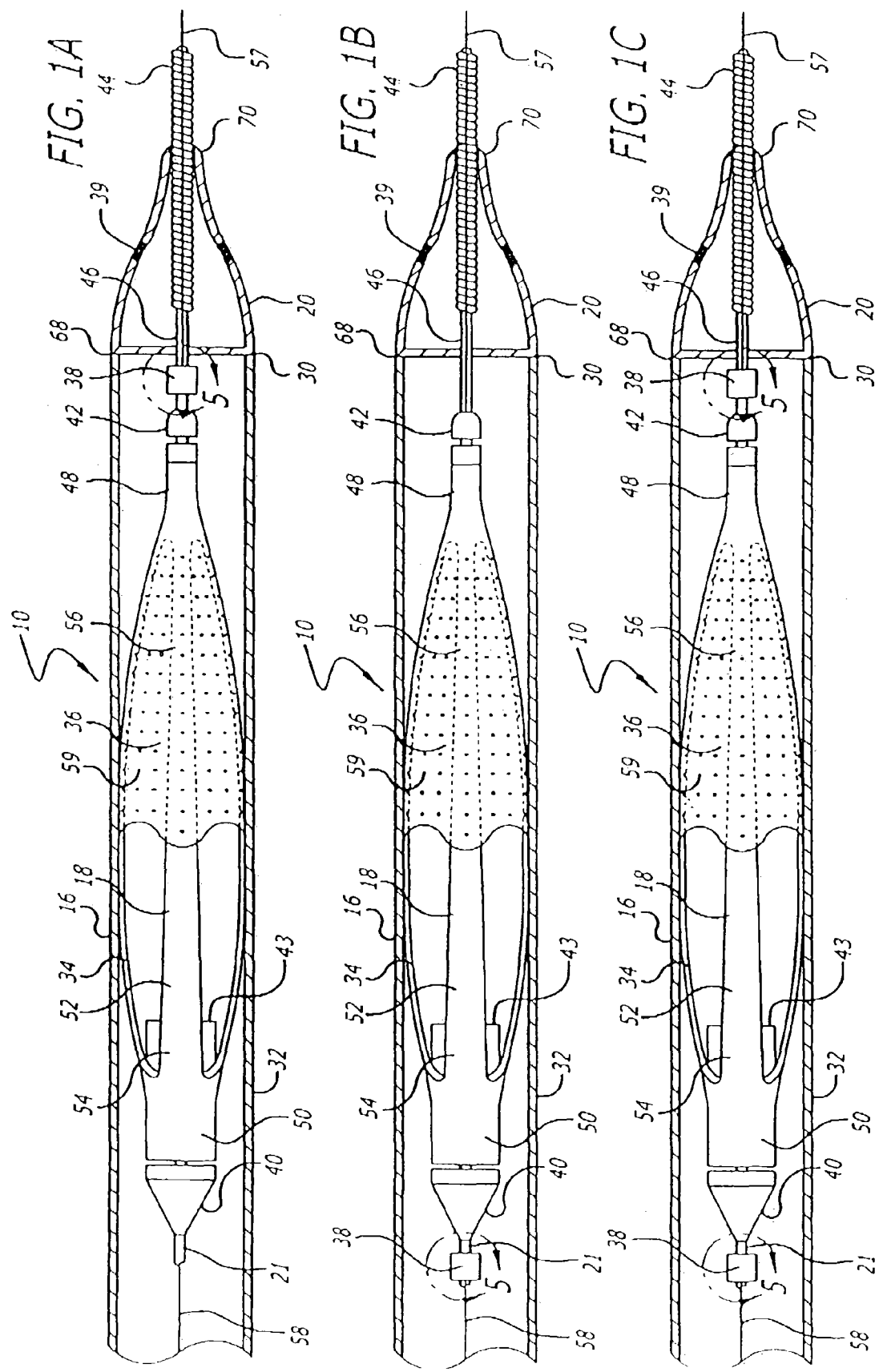

HINGED SHORT CAGE FOR AN EMBOLIC PROTECTION DEVICE

BACKGROUND OF THE INVENTION

This application is a continuation of application Ser. No. 09/944,633 filed Aug. 31, 2001 now U.S. Pat. No. 6,592,606.

The present invention relates generally to improvements in embolic protection systems and methods. In particular, the present invention relates to an improved embolic protection device and system for enabling movement thereof through a patient's tortuous vasculature to a location distal to an interventional procedure site for deployment.

A variety of non-surgical interventional procedures have been developed over the years for opening blood vessels in a patient which are stenosed or occluded by the build up of plaque or other substances on the walls of the blood vessel. Such procedures usually involve the percutaneous introduction of the interventional device into the lumen of the artery, usually through a catheter.

One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Other procedures destroy or remove the plaque build up from the walls of the blood vessel. Laser angioplasty utilizes a laser to ablate the stenosis by super heating and vaporizing the deposited plaque. Atherectomy utilizes a cutting blade which is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge elsewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed, for example, in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to address the problem of debris or fragments entering the circulatory system following treatment by one of the above-identified procedures. One approach has been to cut any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, such systems still present drawbacks since the vacuum catheter may not always remove all of the embolic material from the bloodstream and the powerful suction could cause additional damage to the patient's vasculature.

Techniques which have had some limited success include the placement of an embolic protection device such as a filter or trap downstream from the treatment site to capture embolic debris before it reaches the smaller blood vessels downstream. Such embolic protection devices are adapted to enable the capture of embolic debris which may be released into the bloodstream during the treatment, while still allowing a sufficient amount of oxygenated blood to flow past the device to supply vital organs downstream from the treatment site.

However, there have been problems associated with embolic protection devices, particularly during the expansion, deployment, and formation of the embolic protection device within the blood vessel. The deployment of an embolic protection device may not result in full expansion of the device to properly seal off the circumference of the inner wall of the blood vessel, particularly when the embolic protection device is deployed in tortuous locations having sharp bends. The length of the embolic protection device itself may result in partial collapse of its structure due to lateral loading from the sharp bend in the vessel walls, thereby causing a loss of apposition between the embolic protection device and wall. This can result in embolic material bypassing the filter.

There is a need for an improved system for treating stenosis in body vessels having sharp bends while enabling an embolic protection device to move through a patient's tortuous vasculature to a location distal to an interventional procedure site. Such a system should expand so as to efficiently and effectively seal off the entire circumference of the inner wall of the body vessel, capture embolic material, and prevent embolic material from bypassing the embolic protection device. The system should be relatively easy for a physician to use, while enabling the effective delivery and recovery of a filtering system capable of removing embolic debris released into the bloodstream. The invention disclosed herein satisfies these and other needs.

SUMMARY OF THE INVENTION

The present invention, in general, provides a filtering device for capturing and removing embolic debris from a body vessel and a system for insertion and removal of the filtering device. Embolic debris may be created during the performance of a therapeutic interventional procedure, such as a balloon angioplasty or stenting procedure. The present invention is potentially useful when performing balloon angioplasty, stenting procedures, laser angioplasty or atherectomy in critical body vessels, such as the carotid, renal, and saphenous vein graft arteries, where the release of embolic debris into the bloodstream could possibly occlude the flow of oxygenated blood to the brain or other vital organs which can cause devastating consequences to the patient.

In one aspect, the present invention includes a filtering device. The filtering device is adapted to expand against a body vessel wall to seal off the inner surface thereof, thereby preventing embolic material from bypassing the filtering device and lodging in and blocking body vessels downstream from an interventional procedure site. The filtering device is further adapted for maneuverability through tortuous anatomy having tight bends and for implantation in a curved portion of a body vessel. The present invention is potentially useful for enabling an interventional procedure to be performed in vital arteries, such as the carotid arteries, in which critical downstream body vessels can become blocked with embolic debris, including the main body vessels leading to the brain or other vital organs and in which effective implantation of an embolic protection device is often complicated by sharp bends in the body vessel. As a result, the present invention provides the physician with a higher degree of confidence in the efficient operation of the filtering device for the collection and removal of embolic debris from the body vessel when performing high-risk interventional procedures.

More particularly, the filtering device may have a pre-formed expandable shape and may include a guide wire, a pre-formed expandable basket or cage, filter material, and one or more hinges. The guide wire includes a distal end adapted to be positioned within the body vessel and to extend to a position distal to an interventional procedure site. The pre-formed expandable cage is adapted to engage the distal end of the guide wire and enables the filtering device to expand against and seal off the inner surface of a body vessel wall upon deployment. Filter material attached to the expandable cage facilitates blood flow therethrough while capturing for removal embolic debris released during an interventional procedure. The hinge provides added flexibility to allow the filtering device to be maneuvered through tortuous anatomy and to be deployed in a body vessel having sharp bends without deforming the cage.

Undeformed expansion of the expandable cage precludes the formation of a gap between the filtering device and the body vessel wall, through which embolic material may otherwise flow. The hinge facilitates maneuvering the filtering device through tortuous anatomy by allowing the cage to move independent of the guide wire while still maintaining its connection to the guide wire. Furthermore, the hinge reduces the tendency of the cage to partially collapse when deployed in a body vessel having a sharp bend due to lateral loading from the vessel walls. Moreover, the hinge ensures that the cage will maintain proper wall apposition, thereby providing effective blood filtering and embolic debris capture.

In another aspect, the present invention includes a system for delivering the filtering device through tortuous anatomy, deploying the filtering device in a body vessel at a location distal to an interventional procedure treatment site, and removing the filtering device with the captured embolic material. The system includes a delivery sheath and the aforementioned filtering device adapted to be retained in an unexpanded state by the delivery sheath. An obturator may be provided at the distal end of the guide wire to facilitate maneuvering the system in the patient's vasculature. In one configuration of the present invention, the hinge is located relative to the expandable cage to allow the cage to move independently from the axial direction defined by the portion of the guide wire which is distal to the expandable cage while still maintaining a connection between the cage and guide wire. In this manner, the hinge acts somewhat like a universal joint allowing the free articulation of the expandable cage on the guide wire to provide additional flexibility to the composite cage/guide wire, especially in tight bends in the patient's vasculature. The hinge also allows the effective length of the cage to be reduced, which helps resist the tendency of the cage to partially deform when positioned at sharp bends, thus precluding the formation of a gap between the cage and the body vessel wall. In another configuration of the present invention, a hinge is located so as to allow the cage to move independently from the axial direction defined by the portion of the guide wire which is proximal to the expandable cage while still maintaining a connection between the cage and guide wire. In still another configuration of the present invention, hinges are located so as to allow the cage to move independently from the axial directions defined by both the portion of the guide wire that is proximal to the expandable cage and the portion of the guide wire that is distal to the expandable cage while still maintaining a connection between the cage and guide wire, thereby further reducing the lateral loading on the cage due to sharp bends in the body vessel.

The above objects and advantages of the present invention, as well as others, are described in greater detail in the following description, when taken in conjunction with the accompanying drawings of illustrative embodiments.

BRIEF DESCRIPTION OF THE DRAWINGS

FIG. 1A is an elevational view, partially in section, depicting an embodiment of the present invention having a hinge at the distal side of the filtering device, the filtering device being retained in its unexpanded state by a delivery sheath;

FIG. 1B is an elevational view, partially in section, depicting an embodiment of the present invention having a hinge at the proximal side of the filtering device, the filtering device being retained in its unexpanded state by a delivery sheath;

FIG. 1C is an elevational view, partially in section, depicting an embodiment of the present invention having hinges at both the proximal and distal sides of the filtering device, the filtering device being retained in its unexpanded state by a delivery sheath;

DETAILED DESCRIPTION OF THE PREFERRED EMBODIMENTS

The present invention is directed to an improved filtering device and system for delivering, deploying, and removing the filtering device to facilitate efficient and effective performance of an interventional procedure in a body vessel. The filtering device filters the blood in the body vessel in order to pass blood therethrough while capturing embolic material released into the body vessel during the interventional procedure. Additionally, the filtering device is adapted to enable an expandable cage and filter to freely expand in the body vessel from an unexpanded state. Moreover, the filtering device facilitates placement and deployment of an expandable cage and filter in a body vessel having sharp bends without loss of apposition between the deployed cage and the vessel wall. The system is adapted to facilitate delivery and deployment of the filtering device to a location distal to an interventional procedure site. Additionally, the system is adapted to remove the filtering device and the captured embolic material from the body vessel after the interventional procedure is completed. The embodiments of the improved system are illustrated and described herein by way of example only and not by way of limitation. While the present invention is described in detail as applied to the carotid arteries of the patient, those skilled in the art will appreciate that it can also be used in other body lumens as well, such as the coronary arteries, renal arteries, saphenous veins and other peripheral arteries. Additionally, the present invention can be utilized when performing any one of a number of interventional procedures, such as balloon angioplasty, laser angioplasty or atherectomy.

Figure 2A:
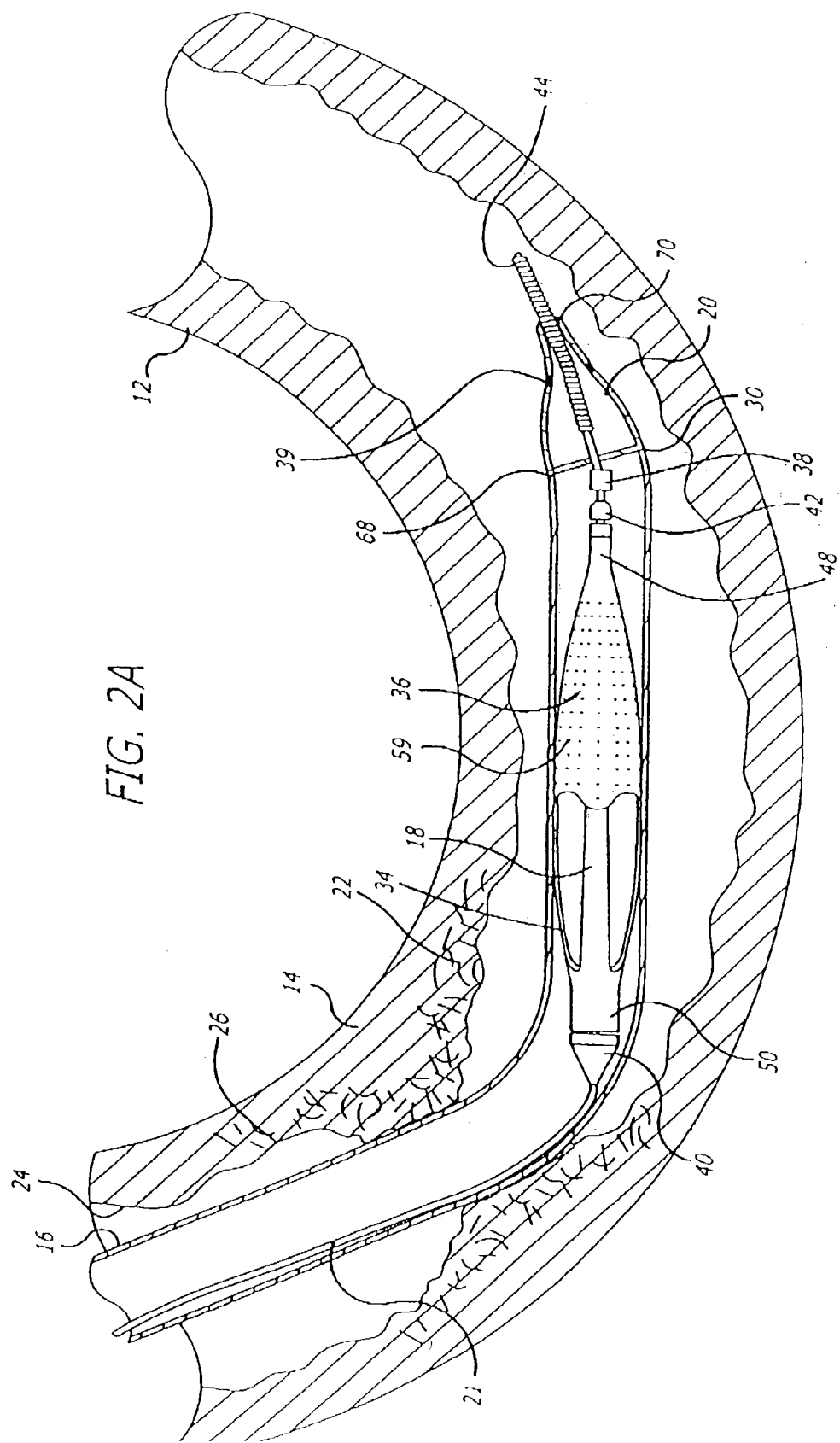
FIG. 2A is an elevational view, partially in section, showing the embodiment of the invention depicted in FIG. 1A disposed within the sharp bend of a body vessel of a patient.
Figure 2B:
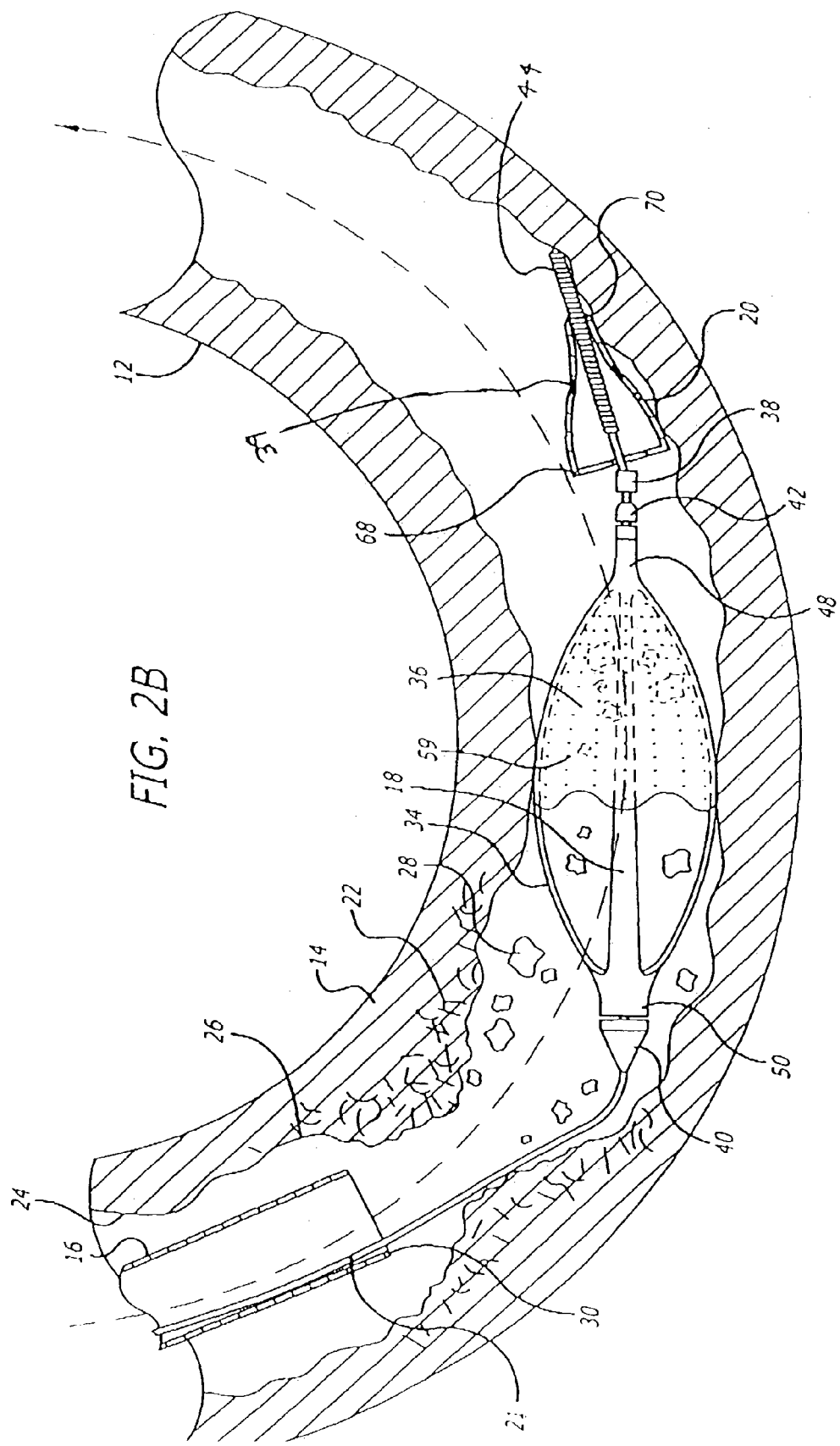
FIG. 2B is an elevational view, partially in section, showing the embodiment of the invention depicted in FIG. 1A with the delivery sheath removed and the filtering device deployed within the sharp bend of a body vessel of a patient.
Figure 3A:
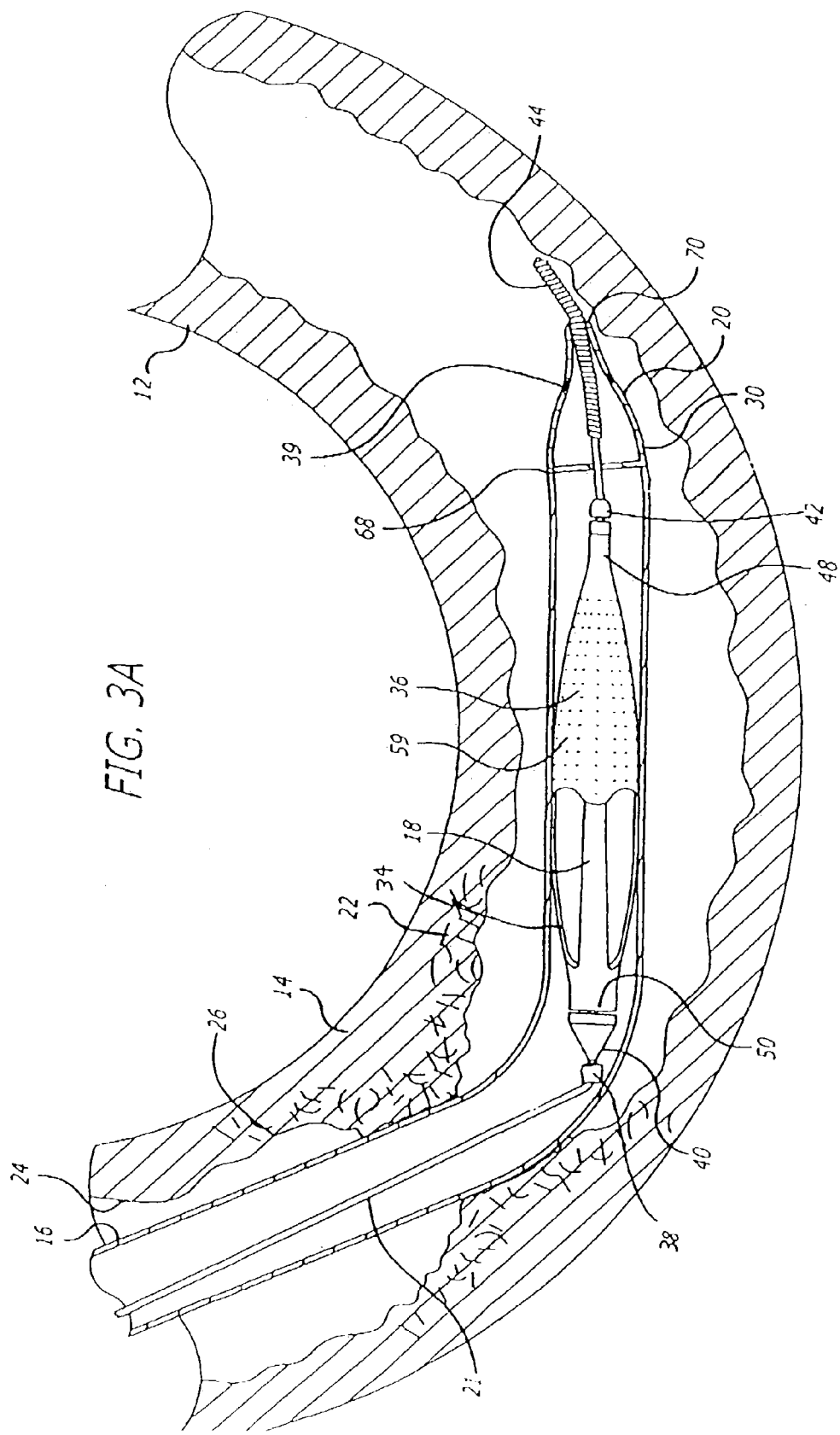
FIG. 3A is an elevational view, partially in section, showing the embodiment of the invention depicted in FIG. 1B disposed within the sharp bend of a body vessel of a patient.
Figure 3B:
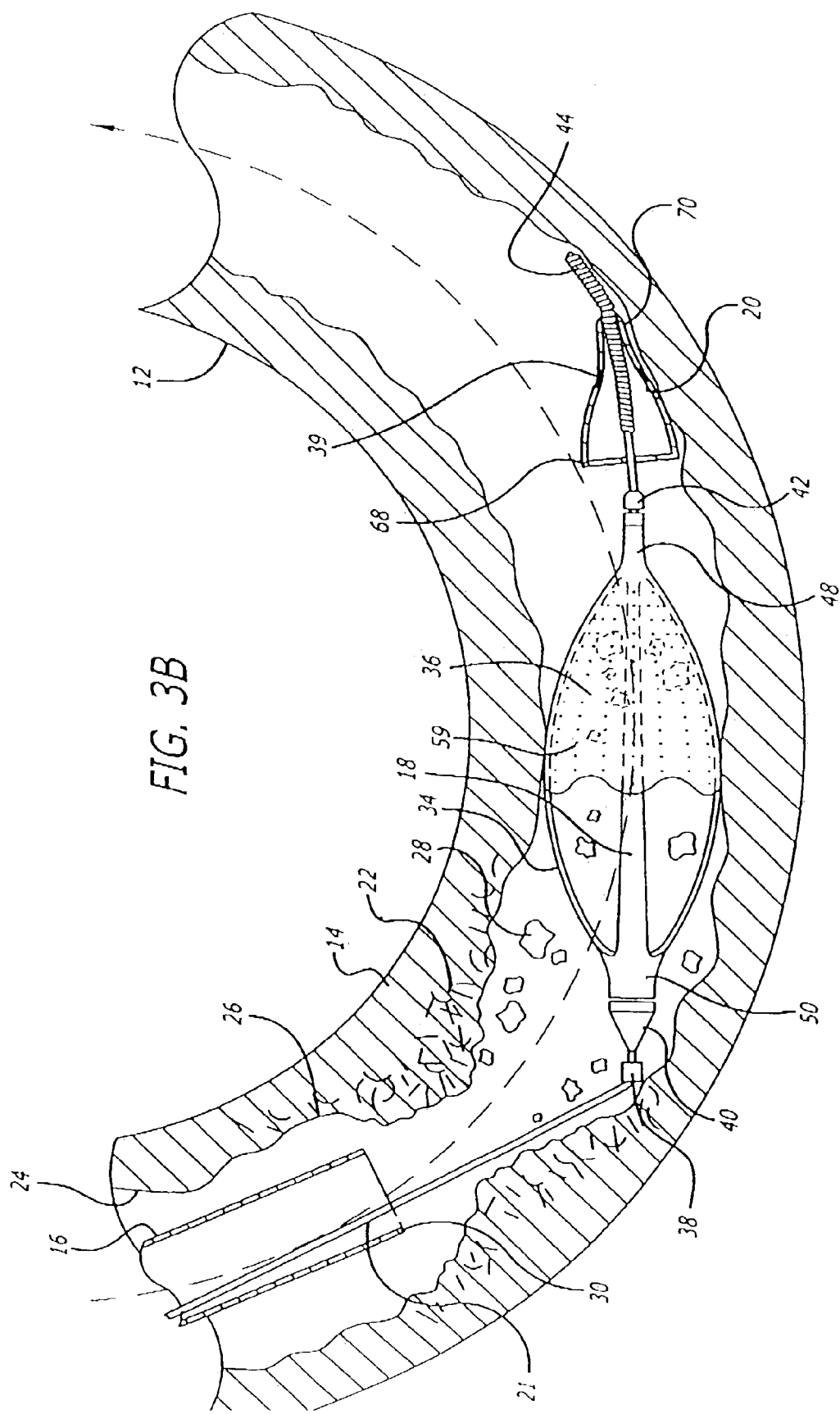
FIG. 3B is an elevational view, partially in section, showing the embodiment of the invention depicted in FIG. 1B with the delivery sheath removed and the filtering device deployed within the sharp bend of a body vessel of a patient.
Figure 4A:
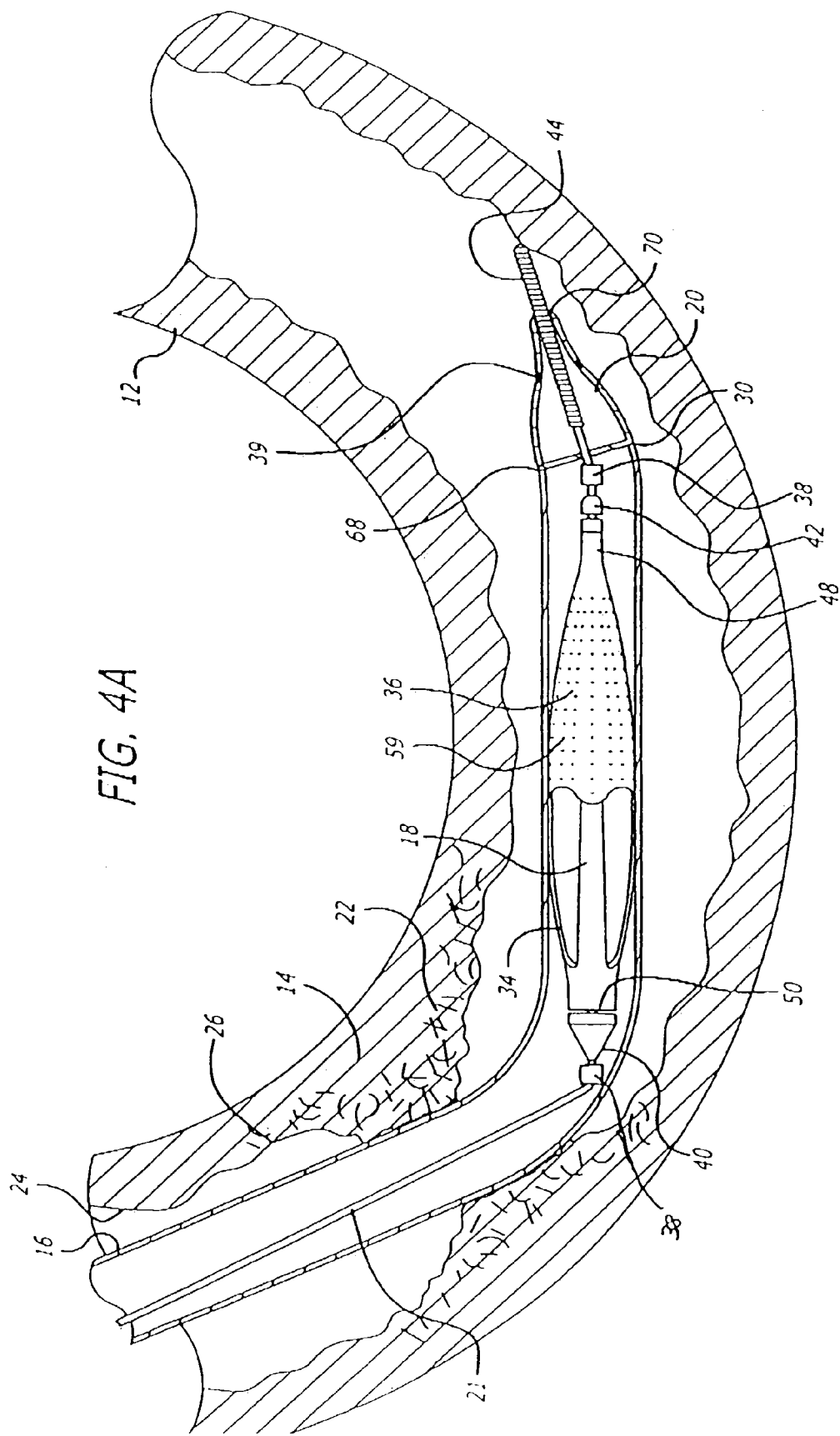
FIG. 4A is an elevational view, partially in section, showing the embodiment of the invention depicted in FIG. 1C disposed within the sharp bend of a body vessel of a patient.
Figure 4B:
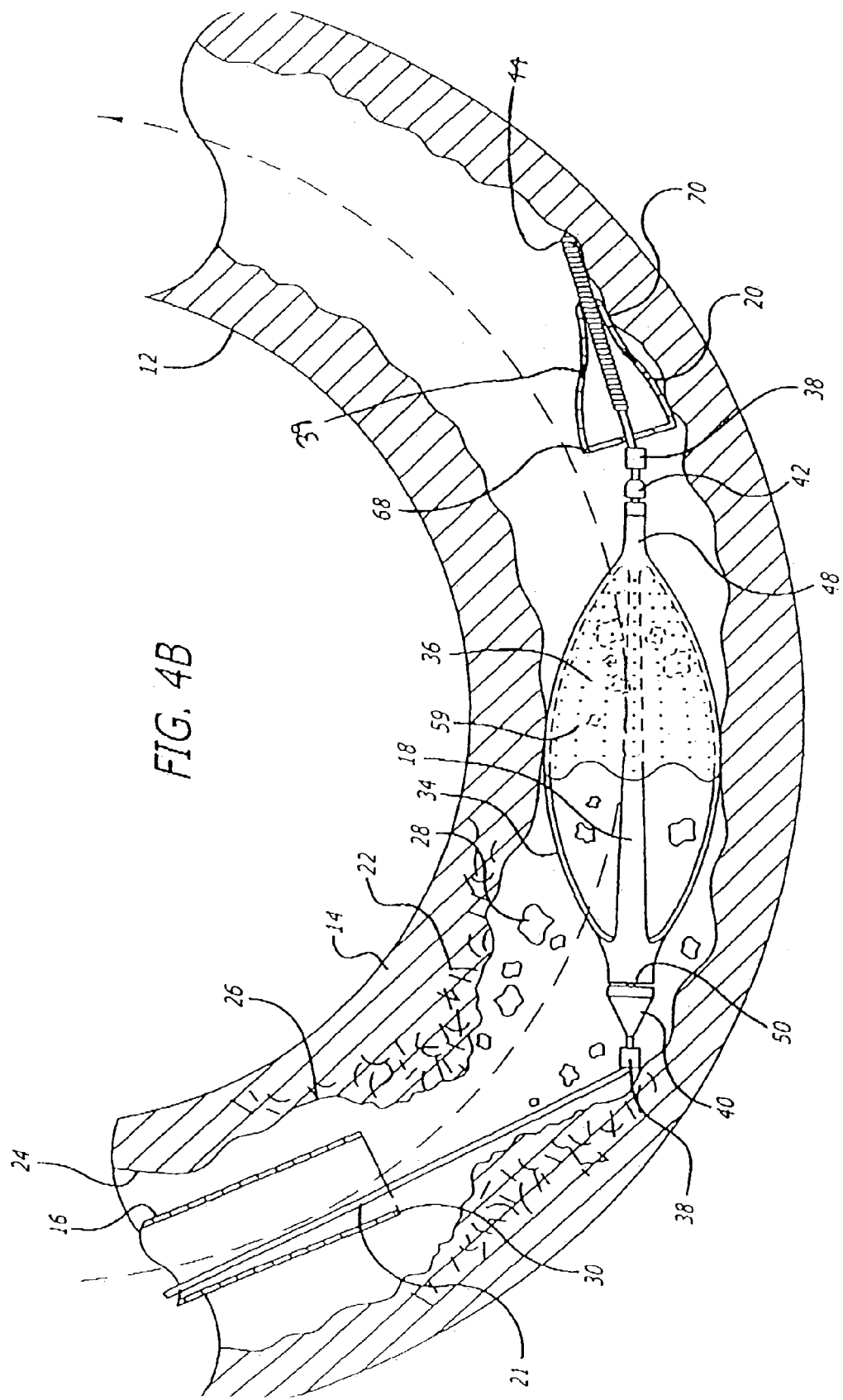
FIG. 4B is an elevational view, partially in section, showing the embodiment of the invention depicted in FIG. 1C with the delivery sheath removed and the filtering device deployed within the sharp bend of a body vessel of a patient.
Figure 5A:
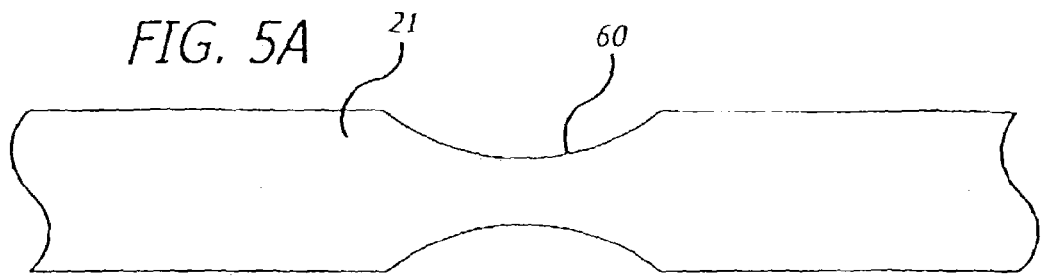
FIG. 5A is an expanded view of the area indicated by dotted lines in FIGS. 1A–1C, depicting a hinge of the present invention formed by cutting notches in the guide wire.
Figure 5B:
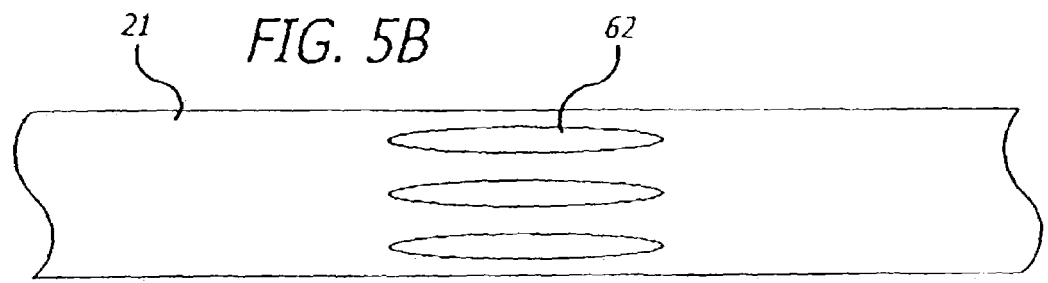
FIG. 5B is an expanded view of the area indicated by dotted lines in FIGS. 1A–1C, depicting a hinge of the present invention formed by incorporating longitudinal slots in the guide wire.
Figure 5C:
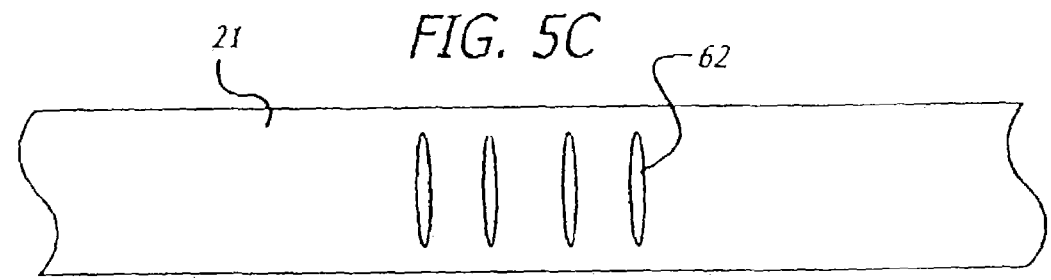
FIG. 5C is an expanded view of the area indicated by dotted lines in FIGS. 1A–1C, depicting a hinge of the present invention formed by incorporating axial slots in the guide wire.
Figure 5D:
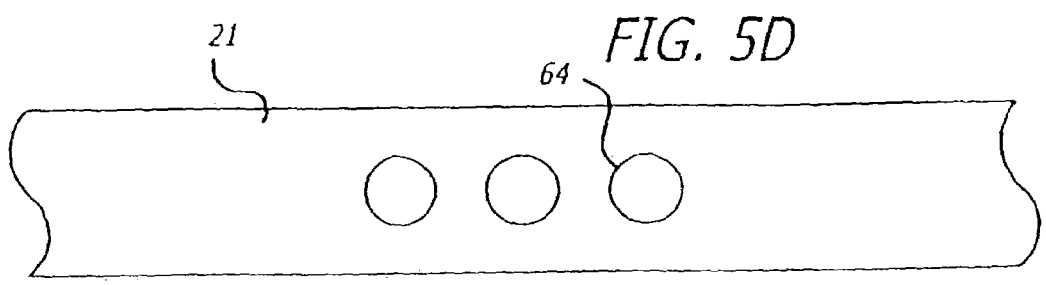
FIG. 5D is an expanded view of the area indicated by dotted lines in FIGS. 1A–1C, depicting a hinge of the present invention formed by incorporating holes in the guide wire.
Figure 5E:
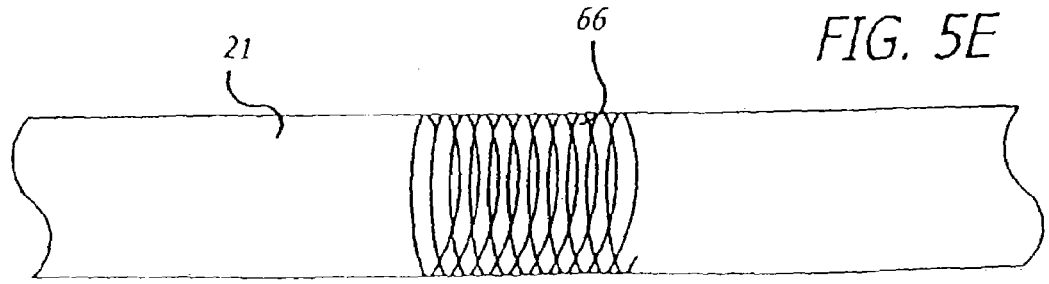
FIG. 5E is an expanded view of the area indicated by dotted lines in FIGS. 1A–1C, depicting a hinge of the present invention formed by incorporating a spring in the guide wire.

Referring to FIGS. 1A–1C, a system 10 is provided for enabling an interventional procedure to be performed in a body vessel 12. The system 10 includes a delivery sheath 16 and a filtering device 18. An obturator 20 may be provided. As shown in FIGS. 2A, 3A and 4A, the filtering device 18 may be retained in an unexpanded state by the delivery sheath 16 and guided into position within a body vessel 12 by a guide wire 21 to facilitate an interventional procedure to be performed at a treatment area 14 having a sharp bend. The treatment area 14 may comprise atherosclerotic plaque 22 which has built up against the inside wall 24 of the body vessel 12 and which decreases the diameter of the artery 26. As a result, blood flow may be diminished through this area. As shown in FIGS. 2B, 3B and 4B, once the filtering device 18 is positioned in the body vessel 12 at a point distal the area of treatment 14, the delivery sheath 16 is retracted and the filtering device 18 expands into apposition with the inside wall 24 of the body vessel 12, thereby filtering the blood flow (shown by the dotted line) and capturing embolic material 28 generated by the interventional procedure. Once the interventional procedure is completed, the filtering device 18 may be retracted into the delivery sheath 16 and the system 10 removed from the patient, thereby removing the captured embolic material 28 from the body vessel 12. Alternately, a separate recovery sheath (not shown) may be used to recover the filtering device 18.

The therapeutic interventional procedure may comprise implanting an expandable interventional instrument (not shown) to compress the build-up of plaque 22 against the inside wall 24 of a body vessel 12 of the patient, such as the carotid artery, and to increase the diameter of the occluded area 14 of the artery 26, thereby restoring sufficient blood flow to the downstream vessels leading to the brain. The expandable interventional instrument not only helps increase the diameter of the occluded area 14, but also may help prevent restenosis at the treatment area 14.

The delivery sheath 16 includes an elongated shaft 32 having a distal portion 30. The delivery sheath 16 may be formed of conventional materials of construction. Preferably, the shaft 32 is made out of a flexible material. Alternately, the shaft 32 can be made out of relatively inelastic materials such as polyethylene, polyvinyl chloride, polyesters and composite materials. The various components may be joined by suitable adhesive or cyanoacrylate based adhesives. Heat shrinking, heat bonding or laser bonding may also be employed where appropriate. Plastic-to-plastic or plastic-to-metal joints can be effected by a suitable acrylonitrile or cyanoacrylate adhesive. Variations can be made in the composition of the materials to vary properties as needed. The expandable interventional instrument may be adapted to be located in the distal portion 30 of the delivery sheath 16 for delivery and expansion at the treatment area 14.

The filtering device 18 expands within the body vessel 12, allowing blood to pass therethrough while capturing embolic material 28 released during the interventional procedure. The filtering device 18 includes a guide wire 21, expandable cage assembly 34, filter material 36, and one or more hinges 38. Stop fittings 40, 42 may be located at the proximal and distal ends of the filtering device 18. The filtering device 18 is adapted to be delivered to a position in the body vessel 12 distal the treatment area 14.

The guide wire 21 facilitates guiding the system 10 through the patient's vasculature past the treatment area 14 and may have a coiled tip 44 at the distal end 46 to provide additional flexibility. The guide wire 21 may be a single continuous piece extending through the expandable cage assembly 34. Alternately, the guide wire 21 may consist of separate distal and proximal sections, each section attached to, but not extending through, the expandable cage assembly 34, thereby reducing the tendency of the expandable cage assembly to deform in sharp bends. The guide wire 21 is typically between one-hundred thirty and three hundred centimeters long and extends two to four centimeters beyond the distal end of the filtering device 18, but it is contemplated that the invention may incorporate other guide wire 21 lengths as may be required.

The expandable cage assembly 34 has a distal end 48 and proximal end 50 which support the filter material 36 while preventing gaps between the filtering device 18 and the inside wall 24 of the body vessel 12 after deployment. The expandable cage assembly 34 is expandable to capture embolic material 28 and collapsible to retain the captured embolic material 28. The expandable cage assembly 34 is adapted to be retained in an unexpanded state by the delivery sheath 16 and expand upon retraction of the delivery sheath 16.

The expandable cage assembly 34 may include a plurality of self-expanding struts 52, each having a proximal portion 54 and a distal portion 56. It should be appreciated that this is just one particular example of an expandable cage assembly which may be used in accordance with the present invention. The expandable cage assembly 34 may be relatively flexible at the distal end 48 and relatively stiff at the proximal end 50, thereby facilitating its maneuverability in the body vessel 12 and its expansion when the delivery sheath 16 is retracted. It is contemplated that the invention may incorporate various forms of self-expanding struts known within the art. It is also contemplated that the plurality of self-expanding struts 52 may each include a radiopaque marker (not shown), thereby enabling verification of the opening or closing of the expandable cage assembly 34. It is further contemplated that the struts 52 may be made of a radiopaque material.

In one particular embodiment, the diameter of the distal end 48 of the expandable cage assembly 34 is less than the diameter of the proximal end 50 of the expandable cage assembly 34, the diameter in the unexpanded state increasing gradually along the length of the expandable cage assembly 34 from the distal end 48 to the proximal end 50. The expandable cage assembly 34 is typically one-and-one-half to three-and-one-half centimeters long and may be tubular-shaped, although it is contemplated that the invention may incorporate various sizes and shapes known within the art. The expandable cage assembly 34 may be comprised of a material, such as NITINOL, having advantageous superelasticity characteristics and which facilitates efficient formation of the expandable cage assembly 34. The expandable cage assembly 34 may be formed by heat treating or any other method known within the art. Radiopaque markers (not shown) may be comprised of platinum or gold bands or any other radiopaque material.

A proximal stop fitting 40 may be mounted on the guide wire 21 at the proximal end 50 of the expandable cage assembly 34 and a distal stop fitting 42 may be mounted on the guide wire 21 at the distal end 48 of the expandable cage assembly 34. The stop fittings 40, 42 have generally conical-shaped end portions for smooth transitions between the expandable cage assembly 34 and guide wire 21 and to provide smooth interfacing surfaces for enabling the expandable cage assembly 34 to rotate while preventing translational movement thereof. Alternately, a stop fitting 43 may be located distal to the proximal end 50 of the expandable cage assembly 34 to prevent the proximal end 50 of the cage from translating longitudinally along the guide wire while allowing the expandable cage assembly 34 to rotate freely thereon. The stop fittings 40, 42 may be secured to the guide wire 21 by a medical grade adhesive, crimping, welding, soldering, or any other method known within the art.

The filter material 36 filters the blood in the body vessel 12, allowing a sufficient amount of blood to flow while preventing embolic material 28 from passing therethrough, and may be defined by a plurality of openings 59. The filter material 36 may be parabolic-shaped, but it is contemplated that the invention can incorporate various filter material shapes known within the art. The filter material 36 may be comprised of polyurethane or any material known within the art having blood filtering capabilities. The filter material 36 may be secured either inside or outside the expandable cage assembly 34 by gluing, heat treating, or any other method known within the art.

A hinge 38 provides additional flexibility and can reduce the effective length of the expandable cage assembly 34, thereby ensuring that proper apposition with the inside wall 24 of the body vessel 12 will be maintained even if the body vessel 12 has a sharp bend. Although the guide wire 21 is flexible, the expandable cage assembly 34 of a filtering device 18 without a hinge 38 may partially collapse due to lateral loading from the body vessel 12 wall 28 when it is deployed in a body vessel 12 having a sharp bend. If the expandable cage assembly 34 partially collapses, apposition with the inside wall 24 of the body vessel 12 may be lost, thereby allowing embolic material 28 to bypass the filter material 36.

It is contemplated that a hinge 38 may be located on the guide wire 21 either at the distal end 48 of the expandable cage assembly 34 as shown in FIG. 1A, at the proximal end 50 of the expandable cage assembly 34 as shown in FIG. 1B, or in both locations as shown in FIG. 1C. These hinges 38 thus allow the distal 48 and/or proximal 50 end of the expandable cage assembly 34 to bend independently from the axial directions 57, 58 defined by the portion of the guide wire 21 that is distal to the expandable cage assembly 34 and the portion of the guide wire 21 that is proximal to the expandable cage assembly 34. This independent movement between the expandable cage assembly 34 and guide wire 21 provides added flexibility and can reduce the effective length of the expandable cage assembly 34 while still maintaining a connection between the expandable cage assembly 34 and guide wire 21. During delivery of the filtering device 18 to the treatment area 14, as shown in FIGS. 2A, 3A and 4A, the added flexibility facilitates maneuvering the system 10 through the patient's vasculature. After deployment of the filtering device 18, as shown in FIGS. 2B, 3B and 4B, the added flexibility facilitates maintaining proper apposition between the expandable cage assembly 34 and the inside wall 24 of the body vessel 12, thereby precluding embolic material 28 from bypassing the filter material 36.

FIGS. 5A–5E show various methods for implementing a hinge 38 on the guide wire 21. By cutting notches 60 (FIG. 5A), slots 62 (FIGS. 5B and 5C), holes 64 (FIG. 5D), or incorporating a spring 66 (FIG. 5E) into the guide wire 21, an area of decreased resistance to bending is created. The guide wire 21 will bend at this area of decreased resistance before additional loading is exerted on the expandable cage assembly 34. It is also contemplated that a hinge 38 may be implemented by using a portion of material of different durometer than the guide wire 21 or other methods known within the art.

The obturator 20 has an outer diameter at the proximal end 68 which is essentially the same as the outer diameter of the delivery sheath 16 and converges to an outer diameter at the distal end 70 which is slightly larger than the outer diameter of the guide wire 21. The obturator 20 is attached to the guide wire 21 such that its distal end 70 covers a portion of the of the guide wire 21 distal end 46 and its proximal end 68 lies distal of any stop fitting 42 or hinge 38 at the distal end 48 of the expandable cage assembly 34. When the filtering device 18 is retained in an unexpanded state by the introducer sheath 16, the introducer sheath 16 distal end 30 and obturator 20 proximal end 68 present a smooth profile for maneuvering the system 10 through the patient's vasculature. The obturator 20 is either partially separated from the expandable cage assembly 34 by a portion of the guide wire 21 (see FIG. 1B) or fully separated from the expandable cage assembly 34 by a hinge 38 (see FIGS. 1A and 1C), thereby allowing the obturator 20 to move independent of the expandable cage assembly 34. Therefore, the effective bending length of the filtering device 18 is further decreased and the tendency of the expandable cage assembly 34 to partially deform in sharp curves is further reduced. It is further contemplated that an obturator hinge 39 may be located on the obturator by utilizing any of the methods shown in FIGS. 5A–5E to create an area of decreased resistance along the circumference of the obturator, thereby allowing the obturator to bend.

In use, the system 10 may be positioned in the patient's vasculature utilizing any of a number of different methods known in the art. In a preferred method, the delivery sheath 16 is placed in the body vessel 12 by utilizing the guide wire 21, which is inserted into the patient's vasculature and manipulated by the physician to the treatment area 14. Once the distal end 30 of the delivery sheath 16 is located distal to the treatment area, the delivery sheath 16 is retracted, thereby allowing the expandable cage assembly 34 to expand. The expansion of the expandable cage assembly 34 is enhanced by the self-expanding struts 52 and radiopaque markers enable verification of expanding or collapsing of the expandable cage assembly 34. After the expandable cage assembly 34 is deployed distal of the treatment area 14, the interventional procedure is performed with the filter material 36 capturing embolic material 28 dislodged during the procedure. After the interventional procedure is completed, the expandable cage assembly 34 is retracted into the delivery catheter 16 or another recovery sheath (not shown), thereby causing the expandable cage assembly 34 and filter material 36, containing the captured embolic material 28, to collapse. The system 10 is then withdrawn from the patient's body vessel 12.

In view of the foregoing, it is apparent that the system and method of the present invention enhances substantially the effectiveness of performing interventional procedures, specifically in body vessels having sharp bends, by maintaining apposition between the expandable filtering device and the wall of the body vessel in which it is deployed, thereby effectively capturing embolic material created during the interventional procedure. Further modifications and improvements may additionally be made to the system disclosed herein without departing from the scope of the invention. Accordingly, it is not intended that the invention be limited, except as by the appended claims.

What is claimed:

1. A filtering device for capturing embolic material released into a body vessel during a therapeutic interventional procedure, comprising:
   a guide wire having a proximal end and a distal end and adapted to be inserted within the vasculature of;
   an expandable cage assembly having distal and proximal ends, the cage assembly being attached to the distal end of the guide wire and expandable to capture embolic material and collapsible to retain the captured embolic material;
   filter material secured to the expandable cage assembly; and
   at least one discrete hinge located on the guide wire proximal to the expandable cage assembly and another hinge located distal to the expandable cage assembly to allow the expandable cage assembly to freely articulate on the guide wire.

2. The filtering device of claim 1, wherein:
   the guide wire does not pass through the expandable cage assembly and comprises separate sections, one section attached to and extending from the proximal end of the expandable cage assembly and one section attached to and extending from the distal end of the expandable cage assembly.

3. The filtering device of claim 1, wherein:
   the at least one hinge comprises notches cut along the longitudinal axis of the guide wire such that an area of decreased guide wire diameter is created.

4. The filtering device of claim 1, wherein:
   the at least one hinge comprises slots cut in the guide wire, each slot extending along the longitudinal axis.

5. The filtering device of claim 1, wherein:
   the at least one hinge comprises slots cut in the guide wire, each slot extending perpendicular to the longitudinal axis.

6. The filtering device of claim 1, wherein:
   the at least one hinge comprises holes cut in the guide wire along the longitudinal axis.

7. The filtering device of claim 1, wherein:
   the at least one hinge comprises a spring connecting separate sections of the guide wire.

8. The filtering device of claim 1, wherein:
   the at least one hinge comprises a portion of material having a different durometer than the guide wire, the portion of material connecting separate sections of the guide wire.

9. The filtering device of claim 1, further comprising:
   stop fittings attached to the guide wire at the proximal and distal ends of the expandable cage assembly, the stop fittings preventing the expandable cage assembly from moving proximally or distally along the guide wire.

10. The filtering device of claim 9, further comprising:
    a third stop fitting attached to the guide wire distal to the proximal end of the expandable cage assembly.

11. The filtering device of claim 10, wherein:
    the three stop fittings are conical-shaped and provide a smooth transition between the expandable cage assembly and guide wire.

* * * * *